United States Patent

Crimmin et al.

[11] Patent Number: 5,652,262
[45] Date of Patent: Jul. 29, 1997

[54] HYDROXAMIC ACID DERIVATIVES AS METALLOPROTEINASE INHIBITORS

[75] Inventors: Michael John Crimmin; Raymond Paul Beckett; Mark Hampton Davis, all of Cowley, United Kingdom

[73] Assignee: British Biotech Pharmaceutical, Ltd., Oxford, England

[21] Appl. No.: 513,868

[22] PCT Filed: Mar. 14, 1994

[86] PCT No.: PCT/GB94/00495

§ 371 Date: Dec. 1, 1995

§ 102(e) Date: Dec. 1, 1995

[87] PCT Pub. No.: WO94/21625

PCT Pub. Date: Sep. 29, 1994

[30] Foreign Application Priority Data

Mar. 16, 1993 [GB] United Kingdom ............... 9305348
Oct. 2, 1993 [GB] United Kingdom ............... 9320360

[51] Int. Cl.⁶ ............... A61K 31/215; C07C 269/00; C07D 271/06; C07D 333/22
[52] U.S. Cl. ............... 514/507; 562/623; 560/158; 549/76; 548/131
[58] Field of Search ............... 562/623; 560/158; 549/76; 548/131; 514/507

[56] References Cited

FOREIGN PATENT DOCUMENTS

| 0236872A3 | 9/1987 | European Pat. Off. |
| 0489579A1 | 6/1992 | European Pat. Off. |
| 0489577A1 | 6/1992 | European Pat. Off. |
| WO/9102716 | 3/1991 | WIPO |

*Primary Examiner*—Joseph Conrad
*Attorney, Agent, or Firm*—Banner & Witcoff, Ltd.

[57] ABSTRACT

Compounds of general formula (I) wherein $R^1$ represents a hydrogen atom or a $C_1$–$C_6$ alkyl, $C_1$–$C_6$ alkenyl, phenyl, phenyl($C_1$–$C_6$)alkyl, $C_1$–$C_6$ alkylthiomethyl, phenylthiomethyl, substituted phenylthiomethyl, phenyl($C_1$–$C_6$)alkylthiomethyl or heterocyclylthiomethyl group; or $R^1$ represents —S—$R^x$ wherein $R^x$ represents a group α; $R^2$ represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl, or cycloalkenyl($C_1$–$C_6$)alkyl; $R^3$ represents an amino acid side chain or a $C_1$–$C_6$ alkyl, benzyl, ($C_1$–$C_6$)alkoxybenzyl, benzyloxy($C_1$–$C_6$)alkyl or benzyloxybenzyl group; $R^4$ represents a hydrogen atom or a methyl group; $R^5$ represents a group $(CH_2)_n A$; or $R^4$ and $R^5$ together represent a group β; Q represents $CH_2$ or CO; m is an integer from 1 to 3; n is an integer from 1 to 6; and A represents a hydroxy, ($C_1$–$C_6$) alkoxy, ($C_2$–$C_7$)acyloxy, ($C_1$–$C_6$)alkylthio, phenylthio, ($C_2$–$C_7$)acylamino or N-pyrrolidone group or a salt and/or N-oxide and/or (where the compound is a thio-compound) a sulphoxide or sulphone thereof have collagenase inhibition activity and are useful in the management of disease involving tissue degradation and/or the promotion of wound healing. Diseases involving tissue degradation include arthropathy (particularly rheumatoid arthritis), inflammation, dermatological diseases, bone resorption diseases and tumour invasion.

20 Claims, No Drawings

HYDROXAMIC ACID DERIVATIVES AS METALLOPROTEINASE INHIBITORS

The present invention relates to therapeutically active hydroxamic acid derivatives, to processes for their preparation, to pharmaceutical compositions containing them, and to the use of such compounds in medicine. In particular, the compounds are inhibitors of metalloproteinases involved in tissue degradation, and are in addition inhibitors of the release of tumour necrosis factor from cells.

BACKGROUND TO THE INVENTION

There is evidence that compounds which have the property of inhibiting the action of metalloproteinases involved in connective tissue breakdown such as collagenase, stromelysin and gelatinase (known as "matrix metalloproteinases", and herein referred to as MMPs) are potentially useful for the treatment or prophylaxis of conditions involving such tissue breakdown, for example rheumatoid arthritis, osteoarthritis, osteopenias such as osteoporosis, periodontitis, gingivitis, corneal, epidermal or gastric ulceration, and tumour metastasis, invasion, and growth.

Metalloproteinases are characterised by the presence in the structure of a zinc(II) ionic site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (J. F. Woessner, FASEB J, 1991,5, 2145–2154). Many known MMP inhibitors are peptide derivatives, based on naturally occuring amino acids, and are analogues of the cleavage site in the collagen molecule. A recent paper by Chapman et al J. Med. Chem. 1993, 36, 4293–4301 reports some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the zinc (II) site in the MMP, and known classes include those in which the zinc binding group is a hydroxamic acid, carboxylic acid, sulphydril, and oxygenated phosphorus (eg phosphinic acid and phosphonic acid) groups.

The following patent publications published prior to the first claimed priority date of this application disclose hydroxamic acid-based MMP inhibitors:

| US 4599361 | (Searle) |
| EP-A-0231081 | (ICI) |
| EP-A-0236872 | (Roche) |
| EP-A-0274453 | (Bellon) |
| WO 90/05716 | (British Bio-technology Ltd ("BBL")) |
| WO 90/05719 | (BBL) |
| WO 91/02716 | (BBL) |
| WO 92/09563 | (Glycomed) |
| EP-A-0497192 | (Roche) |
| WO 92/13831 | (BBL) |
| EP-A-0489577 | (Celltech) |
| EP-A-0489579 | (Celltech) |
| WO 92/22523 | (Research Corporation Technologies) |

The following patent publications published after the first claimed priority date of this application, but before its filing date, also relate to hydroxamic acid-based MMP inhibitors:

| US 6256657 | (Sterling Winthrop) |
| WO 93/09090 | (Yamanouchi) |
| WO 93/09097 | (Sankyo) |
| WO 93/20047 | (BBL) |
| WO 93/21942 | (BBL) |
| WO 93/24449 | (Celltech) |
| WO 93/24475 | (Celltech) |
| EP-A-0574758 | (Roche) |
| WO 94/02446 | (BBL) |
| WO 94/02447 | (BBL) |

The intrinsic potency of compounds within the broad structural groups of hydroxamic derivatives disclosed in the above publications against particular MMPs can be high. For example, many have a collagenase $IC_{50}$ by the in vitro test method of Cawston and Barrett, (Anal. Biochem., 99,340–345, 1979) of less than 50 nM. Unfortunately, however, the pharmacokinetic properties of the specific compounds disclosed in those publications have generally been disappointing. Identifying hydroxamic acid-based MMP inhibitors having a good balance of high intrinsic activity and good pharmacokinetic properties, for example prolonged effective plasma concentrations following oral dosing such that the compounds have high in vivo activity in target diseases or conditions such as rheumatoid or osteoarthritis, or cancer, remains a much sought after goal in the art.

With a few exceptions, the hydroxamic acid derivatives disclosed in the above publications can be regarded as having the following basic structure (IA):

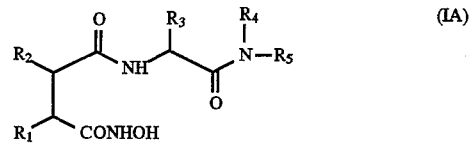

wherein the five substituents $R_1$–$R_5$ may vary according to the detailed disclosure of each publication. The balance of intrinsic level of activity, degree of specificity of activity for a particular category of MMP, and pharmacokinetic properties can vary in an unpredictable way as the substituents $R_1$–$R_5$ are varied.

Tumour necrosis factor (herein referred to as "TNF") is a cytokine which is produced initially as a cell-associated 28 kD precursor. It is released as an active, 17 kD form, which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia: Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

Recently, WO 93/20047 disclosed a class of hydroxamic acid based MMP inhibitors which also are active in inhibiting TNF production.

BRIEF DESCRIPTION OF THE INVENTION

This invention is based on the discovery of a novel group of compounds of general formula (IA), principally characterised in that $R_1$ is an allyl group ($CH_2=CH-CH_2-$), which have a good balance of high intrinsic activity and good pharmacokinetic properties. In particular the compounds produce prolonged effective plasma concentrations following oral dosing (as opposed to a high initial peak concentration followed by relatively rapid exponential decline). The compounds of the invention also have activity as inhibitors of the production of TNF. Such properties imply that the compounds of the invention find particular application in the treatment of diseases and conditions which benefit from prolonged exposure to effective inhibitory concentrations of MMP and/or TNF inhibitors, such as rheumatoid or osteoarthritis, and cancer.

Of the patent publications listed above, only the following claim compounds of formula (IA) in which $R_1$ is an an alkenyl group:

| | |
|---|---|
| WO 90/05716 | (BBL) |
| WO 91/02716 | (BBL) |
| EP-A-0489577 | (Celltech) |
| EP-A-0489579 | (Celltech) |
| WO 93/24449 | (Celltech) |
| WO 93/24475 | (Celltech) |

However, none discloses any specific example of a compound (IA) in which $R_1$ is alkenyl, or the properties expected to be possessed by such compounds. Specifically, none discloses any specific example of a compound (IA) in which $R_1$ is alkenyl. In fact, in all of the compounds of formula (IA) specifically disclosed in EP-A-0489577, EP-A-0489579, WO 93/24449, and WO 93/24475, $R_1$ is hydrogen, while in compounds of formula (IA) disclosed in WO 90/05716 and WO 91/02716 $R_1$ is hydrogen or methyl (or in one instance phenylsulphanylmethyl). Therefore, insofar as the prior art can be regarded as effectively disclosing compounds (IA) in which $R_1$ is alkenyl, it treats $R_1$=alkenyl as equivalent to $R_1$=hydrogen or methyl (and phenylsulphanylmethyl), and has not recognised the activity/bioavailability benefits found by the present inventors to be associated with $R_1$=allyl, the main characterising feature of compounds of the present invention.

DETAILED DESCRIPTION OF THE INVENTION

According to one aspect of the present invention, there is provided a compound of formula (I):

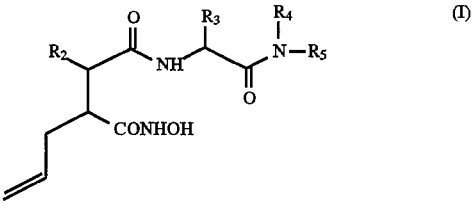

wherein $R_2$ represents a $C_2-C_6$ alkyl group which may contain an ether or thioether linkage;

$R_3$ represents (a) the side chain of a naturally occurring alpha-amino acid in which any carboxylic acid groups may be esterified or amidated, any hydroxyl or thiol groups may be acylated or alkylated (etherified) and any amino groups may be acylated, or (b) a group $R_6(A)_n-$ wherein n is 0 or 1, A represents a divalent $C_1-C_6$ alkyl or $C_2-C_6$ alkenyl group optionally interrupted by one or more $-O-$, or $-S-$ atoms or $-N(R_7)-$ groups where $R_7$ is hydrogen or $C_1-C_6$ alkyl, and $R_6$ is a phenyl or heterocyclyl group either of which may be substituted, or (except where n is 0) a hydrogen atom;

$R_4$ represents hydrogen or methyl;

$R_5$ represents hydrogen, $C_1-C_6$ alkyl or phenyl($C_1-C_6$ alkyl), or a salt, solvate or hydrate thereof.

As used herein the term "$C_1-C_6$ alkyl" refers to a straight or branched chain alkyl moiety having from 1 to 6 carbon atoms, including for example, methyl, ethyl, propyl, isopropyl, butyl, t-butyl, pentyl and hexyl. "$C_2-C_6$ alkyl" of course means straight or branched chain alkyl moiety having from 2 to 6 carbon atoms, and examples include the foregoing, except methyl.

The term "$C_2-C_6$ alkyl group which may contain an ether or thioether linkage" means a group of formula Z—X—Y— wherein Z is $C_2-C_6$ alkyl, X is $-O-$ or $-S-$, Y is a bond or $C_2-C_6$ alkyl, provided that the total number of C atoms does not exceed 5. Examples of such groups include $CH_3(CH_2)_2OCH_2-$, and $CH_3(CH_2)_2S-$.

The term "$C_2-C_6$ alkenyl" refers to a straight or branched chain alkenyl moiety having from 2 to 6 carbon atoms and having in addition one double bond of either E or Z stereochemistry where applicable. This term would include, for example, vinyl, 1-propenyl, 1- and 2-butenyl and 2-methyl-2-propenyl.

As used herein, the term "side chain of a naturally occurring alpha-amino acid" includes the side chains of alanine, arginine, asparagine, aspartic acid, cysteine, cystine, glutamic acid, glycine, histidine, 5-hydroxylysine, 4-hydroxyproline, isoleucine, leucine, lysine, methionine, phenylalanine, proline, serine, threonine, tryptophan, tyrosine, valine, alpha-aminoadipic acid, alpha-amino-n-butyric acid, 3,4-dihydroxyphenylalanine, homoserine, alpha-methylserine, ornithine, pipecolic acid, and thyroxine. The amino acid side chains may be protected; for example the carboxyl groups of aspartic acid, glutamic acid and alpha-aminoadipic acid may be esterified (for example as a $C_1-C_6$ alkyl ester), the amino groups of lysine, ornithine, 5-hydroxylysine, 4-hydroxyproline may be convened to amides (for example as a $COC_1-C_6$ alkyl amide) or carbamates (for example as a C(=O)OC$_1$-C$_6$ alkyl or C(=O)OCH$_2$Ph carbamate), the hydroxyl groups of 5-hydroxylysine, 4-hydroxyproline, serine, threonine, tyrosine, 3,4-dihydroxyphenylalanine, homoserine, alpha-methylserine and thyroxine may be convened to ethers (for example a C$_1$-C$_6$ alkyl or a (C$_1$-C$_6$ alkyl)phenyl ether) or esters (for example a C(=O)C$_1$-C$_6$ alkyl ester) and the thiol group of cysteine may be converted to thioethers (for example a C$_1$-C$_6$ alkyl thioether) or thioesters (for example a C(=O)C$_1$-C$_6$ alkyl thioester).

The unqualified term "heterocyclyl" refers to a 5–7 membered heterocyclic ring containing one or more heteroatoms selected from S, N and O, and optionally fused to a benzene ring, including for example, pyrrolyl, furyl, thienyl, imidazolyl, oxazolyl, oxadiazolyl, thiazolyl, pyrazolyl, isoxazolyl, triazolyl, thiadiazolyl, pyridazinyl, pyrazinyl, triazinyl, pyridinyl, pyrrolidinyl, pyrimidinyl, morpholinyl, piperizinyl, indolyl, benzimidazole, phthalimido, 1,2-dimethyl-3,5-dioxo-1,2,4-triazolidin-4-yl, 3-methyl-2,5-dioxo-1-imidazolidinyl and 3,4,4-trimethyl-2,5-dioxo-1-imidazolidinyl.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

Unless otherwise specified in the context in which it occurs, the term "substituted" as applied to any moiety herein means substituted with up to four substituents, each of which independently may be C$_1$-C$_6$ alkoxy, hydroxy, thio, C$_1$-C$_6$ alkylthio, amino, halo (including fluoro, chloro, bromo and iodo), trifluoromethyl, nitro, —COOH, —CONH$_2$ or —CONHR$^A$ wherein R$^A$ is a C$_1$-C$_6$ alkyl group or the residue of a natural alpha-amino acid.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the allyl group and hydroxamic acid moiety —S,

C atom carrying the R$_2$ group —R,

C atom carrying the R$_3$ group —S, but mixtures in which the above configurations predominate are also contemplated.

Presently preferred compounds include those in which, independently or in any combination:

R$_2$ represents an isobutyl group;

R$_3$ represents a phenylmethyl (benzyl) group in which the phenyl ring is optionally substituted with a C$_1$–C$_4$ alkoxy or HOOC—(C$_1$–C$_4$ alkyl)—O— group, a thienylmethyl group, a C$_1$–C$_6$ alkyl group for example a tertbutyl or isobutyl group, or a CH$_2$CO$_2$ (C$_1$–C$_4$)alkyl or CH$_2$CH$_2$CO$_2$ (C$_1$–C$_4$)alkyl group;

R$_4$ represents a hydrogen atom;

R$_5$ represents a (C$_1$–C$_4$)alkyl group or a benzyl group;

Interesting compounds of the invention are:

3R-(3-methoxycarbonyl-1S-methylcarbamoyl-propylcarbamoyl )-5-methyl-2S-2-propenyl-hexanohydroxamic acid;

3R-(1S-methylcarbamoyl-2-thien-2-yl-ethylcarbamoyl)-5-methyl-2S-2-propenyl-hexanohydroxamic acid;

3R-(3-Methyl-1S-methylcarbamoyl-butylcarbamoyl)-5-methyl-2S-2-propenyl-hexanohydroxamic acid;

2S-[1S-methylcarbamoyl-2-oxadiazol-5-yl-ethylcarbamoyl)-5-methyl-2S-2-propenyl-hexanohydroxamic acid;

and salts, solvates or hydrates thereof.

A compound of the invention which is preferred for its high intrinsic activity, and for its good pharmacokinetic properties, evidenced for example by its high in vivo activity following oral administration in a standard rat adjuvant arthritis model, is:

3R-(2-phenyl-1S-methylcarbamoyl-ethylcarbamoyl)-5-methyl-2S-2-propenyl -hexanohydroxamic acid and its salts, solvates or hydrates.

A further compound of the invention which is especially preferred for its high intrinsic activity, and for its good pharmacokinetic properties, evidenced for example by its prolonged high plasma concentrations following oral administration, is:

3R-(2,2-dimethyl-1S-methylcarbamoyl-propylcarbamoyl)-5-methyl-2S-2-propenyl-hexanohydroxamic acid and its salts, solvates or hydrates.

Another compound of the invention which is preferred for its good intrinsic activity in inhibiting especially stromelysin, is:

3R-(2-phenyl-1S-phenylmethylcarbamoyl-ethylcarbamoyl)-5-methyl-2S-2-propenyl-hexanohydroxamic acid and its salts, solvates or hydrates.

Compounds according to the present invention may be prepared by methods known per se in the art, and by the following process, which forms another aspect of the invention, namely a process for the preparation of a compound of formula (I) comprising:

(a) coupling an acid of general formula (II)

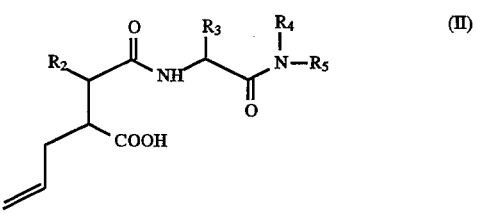

or an activated derivative thereof with hydroxylamine, O-protected hydroxylamine, or a salt thereof, R$_2$, R$_3$, R$_4$, and R$_5$ being as defined in general formula (I) except that any substituents in R$_2$, R$_3$, R$_4$, and R$_5$ which are potentially reactive with hydroxylamine, O-protected hydroxylamine or their salts may themselves be protected from such reaction, then removing any protecting groups from the resultant hydroxamic acid moiety and from any protected substituents in R$_2$, R$_3$, R$_4$, and R$_5$; and (b) optionally converting a compound of general formula (I) into another compound of general formula (I).

Conversion of (II) to an activated intermediate such as the pentafluorophenyl, hydroxysuccinyl, or hydroxybenztriazyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily clearable ethers such as the t-butyl or benzyl ether, or as readily cleavable esters such as the acetate. Carboxy groups are often protectable as readily clearable esters, such as the t-butyl or benzyl ester.

A compound of general formula (II) can be prepared by coupling an acid of formula (III) or an activated derivative thereof with an amine of formula (IV)

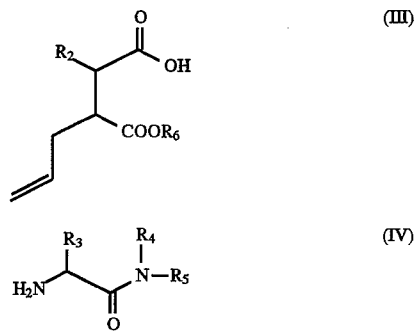

wherein $R_2$, $R_3$, $R_4$, and $R_5$ are as defined in general formula (I) and $R_6$ represents $C_1$-$C_6$ alkyl (eg t-butyl), or benzyl. Active derivatives of acids (III) include activated esters such as the pentafluorophenyl ester, acid anhydrides and acid halides, eg chlorides.

As mentioned above, compounds of formula (I) are useful in human or veterinary medicine since they are active as inhibitors of MMPs. A further advantage of the compounds of formula (I) lies in their ability to inhibit the release of tumour necrosis factor (TNF) from cells.

TNF is a cytokine which is produced initially as a cell-associated 28 kD precursor, is released as an active, 17 kD form (Jue, D-M et al., (1990) Biochemistry 29:8371–8377), which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal. There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Preventing the production or action of TNF is, therefore, predicted to be a potent therapeutic strategy for many inflammatory, infectious, immunological or malignant diseases. These include, but are not restricted to, septic shock, haemodynamic shock and sepsis syndrome (Mathison et al. (1988) J. Clin. Invest. 81:1925–1937; Miethke et al. (1992) J. Exp. Med. 175:91–98), post ischaemic reperfusion injury, malaria (Grau et al. (1989) Immunol. Rev. 112:49–70); mycobacterial infection (Barnes et al. (1992)Infect. Imm. 60:1441–6), meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

It has recently been shown that the effects of TNF are mediated by two peptides, TNF α and TNF β. Although these peptides have only 30% homology with each other, they activate the same receptors and are encoded by immediately adjacent genes. As used herein, the term tumour necrosis factor or TNF therefore means tumour necrosis factor α and peptides having a high degree of sequence homology with, or substantially similar physiological effects to, TNF α, for example TNF β.

Accordingly in another aspect, this invention concerns:

(i) a method of management (by which is meant treatment or prophylaxis) of diseases or conditions mediated by MMPs and/or TNF in mammals, in particular in humans, which method comprises administering to the mammal an effective amount of a compound of formula (I) above, or a pharmaceutically acceptable salt thereof; and (ii) a compound of formula (I) for use in human or veterinary medicine, particularly in the management (by which is meant treatment or prophylaxis) of diseases or conditions mediated by MMPs and/or TNF; and (iii) the use of a compound of formula (I) in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compound of formula (I) together with a pharmaceutically or veterinarily acceptable excipient or carrier.

One or more compounds of general formula (I) may be present in the composition together with one or more excipient or carrier.

The compounds with which the invention is concerned may be prepared for administration by any route consistent with their pharmacokinetic properties. The compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats;

emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of general formula I. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The examples which follow serve to illustrate the invention but are not intended to limit the scope in any way. The amino acids used in the examples were commercially available or were prepared according to literature procedures.

The following abbreviations have been used throughout:

| | |
|---|---|
| DIPE | Diisopropyl ether |
| DMF | N,N-Dimethylformamide |
| HOBt | 1-Hydroxybenzotriazole |
| LDA | Lithium bis(trimethylsilyl)amide |
| NMM | N-Methylmorpholine |
| THF | Tetrahydrofuran |
| TFA | Trifluoroacetic acid |
| TLC | Thin layer chromatography |
| EDC | N-Ethyl-N'-(3-dimethylaminopropyl)carbodiimide hydrochloride |

$^1$H and $^{13}$C NMR spectra were recorded using a Bruker AC 250E spectrometer at 250.1 and 62.9 MHz, respectively. NMR data are recorded as ppm. Elemental microanalyses were performed by CHN Analysis Ltd., Alpha House, Countesthorpe Road, South Wigston, Leicester LE8 2PJ, UK. Specific rotation data are recorded as g/ml.

Preparation of Intermediate 1

3R,S-Allyl-2R-isobutyl-1,4-dioic acid-1-pentafluorophenyl-4 tert-butyl diester (3:1, RS:RR).

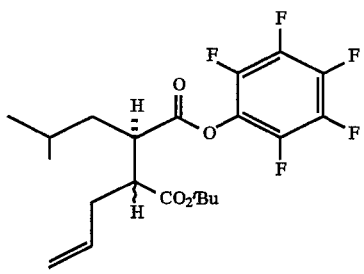

Step 1

N-(4-Methylpentanoyl)-4S-phenylmethyl-oxazolidin-2-one

A dry 500 ml flask equipped with a magnetic stirrer was charged with 4S-phenylmethyl-oxazolidin-2-one (17.72 g, 100 mmol), this was capped with a rubber septum and flushed with nitrogen. Anhydrous THF (300 ml) was added via a cannula and the resulting solution was cooled to $-78°$ C. in an acetone/dry-ice bath. A solution of 1.47M n-butyllithium in hexane (68.4 ml, 101 mmol) was transferred via cannula to a dry, septum-stoppered 100 ml dropping funnel. This was added dropwise to the THF solution over 10 minutes.

4-Methylvaleric acid chloride (14.80 g, 110 mmol) was added in one portion by syringe after completion of the addition of n-butyllithium. The resulting solution was stirred at $-78°$ C. for 30 minutes and then allowed to warm to ambient temperature over 30 minutes. Excess acid chloride was quenched by the addition of aq. NH$_4$Cl (60 ml) and the bulk of the solvent was removed under reduced pressure. The resulting slurry was extracted with dichloromethane (2×80 ml). The combined organic extracts were washed with 1M NaOH (75 ml), brine (75 ml), dried (Na$_2$SO$_4$ anhyd.) and filtered. The solvent was removed to yield a yellow oil (29.20 g, crude). $^1$H-NMR; d (CDCl$_3$), 7.34–7.19 (5H, m), 4.73–4.63 (1H, m), 4.25–4.16 (2H, m), 3.30 (1H, dd, J=3.3 Hz), 3.05–2.85 (2H, m), 2.78 (1H, dd, J=9.5 Hz), 1.76–1.53 (3H, m) and 0.97 (6H, d, J=6.2 Hz).

Step 2

N-(4-(tert-Butyl)-2R-isobutyl-butan-1,4-dioyl)-4S-phenylmethyl-oxazolidin-2-one

N-(4-Methylpentanoyl)-4S-phenylmethyl-oxazolidin-2-one (20 g, 72.6 mmol) was placed in a dry 1 liter 3-necked flask to which was added dry THF (400 ml). The mixture was kept under a stream of argon and cooled to $-78°$ C. (dry ice/acetone). Sodium bis(trimethyl)silylamide (1M solution in THF, 72.6 ml, 72.6 mmol) was added dropwise through a dropping funnel. After stirring for 20 minutes, tert-butyl bromoacetate (21.02 g, 15.8 ml, 109 mmol) was added dropwise over 1 minute, to give an orange solution. The mixture was kept at $-78°$ C. and allowed to warm to $-50°$ C. over 2 hours. The reaction was then quenched by adding acetic acid (10.90 g, 10.4 ml, 182 mmol) in ether (50 ml) at $-50°$ C., whereupon the solution became colourless. The solvent was removed under reduced pressure and the resulting slurry was partitioned between ethyl acetate and brine. The ethyl acetate layer was washed once with brine and the original brine layer was back-extracted with ethyl acetate. The combined organic layers were dried, filtered and the solvent removed, giving a yellow oil which crystallised on cooling overnight to yield the title compound as a crystalline solid (21.36 g, 76%). $^1$H-NMR; d (CDCl$_3$), 7.38–7.24 (5H, m), 4.62–4.72 (1H, m), 4.35–4.20 (1H, m), 4.18–4.16 (2H, m), 3.36 (1H, dd, J=3.25 Hz), 2.72 (1H, dd, J=2.3 Hz), 2.49 (1H, dd, J=4.6 Hz), 1.72–1.24 (3H, m), 1.44 (9H, s) and 0.91–0.96 (6H, dd, J=4.5 Hz). $[a\alpha]^{25}_D$=+66.9° (c=1, MeOH).

Step 3

2R-Isobutyl-butan-1,4-dioic acid-4-tert-butyl ester

N-(4-(tert-Butyl)-2R-isobutyl-butan-1,4-dioyl)-4S-phenylmethyl-oxazolidin-2-one (15.30 g, 39 mmol) was placed in a 1 liter flask with a stirrer bar and to it was added a mixture of THF (600 ml) and water (150 ml). The solution was stirred and cooled to 0° C. (ice/acetone bath) then 60% aq. H$_2$O$_2$ (4.5 ml, 157 mmol) was added via syringe over 5 minutes, followed by LiOH (2.65 g, 63 mmol) in 100 ml water. The reaction mixture was stirred for 1 h at 0° C. TLC (10% methanol in dichloromethane) showed complete reaction (product gave a yellow spot on TLC on staining with bromocresol green and heating). The reaction mixture was quenched with NaNO$_2$ (10.88 g, 157 mmol) so that the final pH was 12–13. THF was removed in-vacuo and the aqueous layer was extracted with dichloromethane (3×200 ml) to recover the chiral auxiliary. The organic extracts were dried (MgSO$_4$ anhyd.), filtered and the solvent removed in-vacuo and the resulting solid chiral auxiliary (7.05 g, 39 mmol, 100%) recrystallised from ethyl acetate-hexane (2:1). $[a]^{25}_D$=−13.0° (c=1, MeOH).

The aqueous layer was cooled in an ice bath and acidified to pH 5–6 with 2M HCl. The resulting cloudy solution was extracted with ethyl acetate (4×200 ml), readjusting the pH to 5–6 in between extractions. The combined organic extracts were dried over MgSO$_4$, filtered and the solvent was removed to yield the title compound as a pale yellow oil (8.21 g, 91%). $^1$H-NMR; δd (CDCl$_3$), 2.85 (1H, m), 2.59 (1H, dd, J=16, 9 Hz), 2.38 (1H, dd, J=16, 5 Hz), 1.64 (1H, m), 1.28 (1H, m) and 0.93 (6H, dd, J=7, 8 Hz). $[a]^{25}_D$=+10.4° (c=1, MeOH).

Step 4

3R,S-Allyl-2R-isobutyl-butan-1,4-dioic acid-4-tert-butyl ester (1:9, RS:RR)

To a stirred solution of 2R-isobutyl-1,4-dioic acid-4-tert-butyl ester (5 g, 21.7 mmol) in dry THF (100 ml), under an argon atmosphere, at −78° C., was added 1.5M LDA (31.8 ml, 47.74 mmol) dropwise via cannula. After stirring the solution at −78° C. for 1 hour, allyl bromide (2.44 ml, 28.21 mmol) was added dropwise via syringe. The resulting solution was allowed to warm to room temperature over a 2 hour period. Methanol (10 ml) was added and the solution was stirred at room temperature. After 30 minutes the reaction mixture was concentrated under reduced pressure. The residue was taken up in dichloromethane (100 ml) and washed with 1M HCl (100 ml) and brine (100 ml). The dichloromethane layer was dried over MgSO$_4$, filtered and solvent removed under reduced pressure to give the title compound as a golden oil (5.6 g, 96.7%) (1:9, RS:RR) $^1$H-NMR; d (CDCl$_3$, major diastereoisomer), 5.78–5.63 (1H, m), 5.01–5.11 (2H, m), 2.57–2.72 (2H, m), 2.37 (2H, m), 1.52–1.67 (2H, m), 1.42 (9H, s), 1.37 (1H, m) and 0.90 (6H, d, J=6.3 Hz). $^{13}$C-NMR; d (CDCl$_3$, major diastereoisomer) 181.1, 172.9, 134.6, 117.3, 81.2, 47.8, 44.3, 38.4, 27.9, 25.9, 23.5, and 21.5.

Step 5

3R,S-Allyl-2R-isobutyl-1,4-dioic acid-4-tert-butyl ester (3:1, RS:RR)

(i) To a stirred solution of 3R,S-Allyl-2R-isobutyl-1,4-dioic acid-4-tert-butyl ester (1:9, RS:RR) (5.11 g, 18.9 mmol) in dry THF (100 ml) under argon at −78° C. was added 1.5M LDA (27.7 ml, 41.6 mmol) via cannula. The reaction mixture was warmed to room temperature over a 2 hour period then cooled back to −78° C. and methanol (8 ml) was added via syringe. The reaction was then allowed to warm to room temperature for a further 2 hours. The solvent was removed under reduced pressure. The residue was taken up in dichloromethane (150 ml) and washed with 1M HCl (150 ml) and brine (150 ml). The dichloromethane layer was added over MgSO$_4$, filtered and the solvent removed under reduced pressure to yield the title compound (3:2, RS:RR), as a brown oil (4.7 g, 92%).

(ii) Utilising the epimerisation procedure described in Example 3b(i), but employing a reaction temperature of −78° C. after addition of LDA in lieu of allowing the reaction mixture to warm to room temperature yielded the title compound as a brown oil (4.6 g, 98%) (3:1, RS:SR). $^1$H-NMR; d (CDCl$_3$, major diastereoisomer), 11.60 (1H, br s), 5.75–5.61 (1H, br m), 5.06–4.96 (2H, br m), 2.70–2.52 (2H, br, m), 2.36–2.19 (2H, br m), 1.65–1.44 (2H, br m), 1.40 (9H, s), 1.13 (1H, m) and 0.86 (6H, dd, J=4.4, 2.1 Hz). $^{13}$C-NMR; d (CDCl$_3$, major diastereoisomer) 180.7, 172.2, 134.6, 117.1, 81.0, 48.6, 45.7, 38.9, 34.8, 33.4, 27.9, 26.2 and 21.2.

Step 6

3R,S-Allyl-2R-isobutyl-1,4-dioic acid-1-pentafluorophenyl-4 tert-butyl diester (3:1, RS:RR)

To a stirred solution of 3R,S-Allyl-2R-isobutyl-1,4-dioic acid-4 tert-butyl ester (4.60 g, 17.2 mmol) (3:1, RS:RR)in dichloromethane (50 ml) was added pentafluorophenyl (6.13 g, 33.3 mmol). The reaction mixture was cooled to 0° C. and NMM (2.02 g, 20.0 mmol) and EDC (3.94 g, 20.0 mmol) were added. The reaction mixture was allowed to warm to room temperature and stirred for 12 hours then the solvent was removed under reduced pressure. The residue was taken up in dichloromethane (50 ml) and washed with 1M HCl (3×50 ml), saturated sodium bicarbonate (3×50 ml) and brine (50 ml). The dichloromethane layer was dried over MgSO$_4$, filtered and the solvent removed under reduced pressure to give a brown oil. Column chromatography (flash silica, dichloromethane) yielded the title compound as a golden oil (5.47 g, 74%) (3:1, RS:SR). $^1$H-NMR; d (CDCl$_3$, major diastereoisomer), 5.85–5.67 (1H, br m), 5.17–5.05 (2H, br m), 3.10–3.01 (1H, m), 2.79–2.69 (1H, m), 2.51–2.29 (2H, br m), 1.88–1.61 (2H, br m), 1.46 (9H, s), 1.37–1.24 (1H, m) and 0.96 (6H, dd, J=4.0, 4.5 Hz). $^{13}$C-NMR; d (CDCl$_3$, major diastereoisomer), 171.5, 170.3, 134.1, 117.5, 81.4, 48.8, 45.8, 39.5, 35.0, 27.9, 26.3, 23.5, and 21.0.

EXAMPLE 1

3R-(2-Phenyl-1S-methylcarbamoyl-ethylcarbamoyl)-5-methyl-2S-2-propenyl-hexanohydroxamic acid

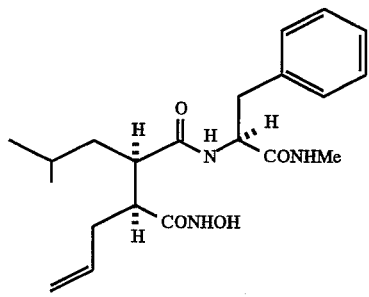

EXAMPLE 1a

3R,S-(2-Phenyl-1S-methylcarbamoyl-ethylcarbamoyl)-5-methyl-2S-2-propenyl-hexanoic acid-4-tert-butyl ester A solution of 3R,S-allyl-2R-isobutyl-succinic acid 4-tert-butyl 1-pentafluorophenyl diester (7.0 g, 16.0 mmol) (3:1, RS:RR) and S-phenylalanine methylamide (3.72 g, 20.9 mmol) in DMF (70 ml) was stirred at 45° C. for 8 hours and at room temperature for 24 hours. The DMF was removed under reduced pressure. The residue was taken up in dichloromethane (50 ml) and washed with sodium carbonate (1M, 2×150 ml), 1M HCl (2×150 ml) and brine (150 ml). The dichloromethane layer was dried over $MgSO_4$, filtered and the solvent was removed under reduced pressure to give a golden oil. Column chromatography (flash silica; 1:1 ethyl acetate: hexane) yielded the title compound as a white solid after recrystallisation from ethyl acetate/hexane (10:1 diastereomer ratio, 4.05 g, 59%). $^1$H-NMR; $\delta(CDCl_3$, major diastereoisomer), 7.29 to 7.21 (5H, m), 6.35 (1H, d, J=7.6 Hz), 5.94 (1H, br s), 5.69 to 5.52 (1H, br m), 4.98 (1H, s), 4.93 (1H, d, J=7.7 Hz), 4.64 (1H, d, J=7.4 Hz), 3.07 (2H, d, J=7.4 Hz), 2.72 (3H, d, J=1.7 Hz), 2.52 to 2.30 (2H, br m), 2.05 to 180)2H, br m), 1.62 (1H, m), 1.43 (10H, s and m), 1.87 (1H, m), and 0.84 (6H, dd, J=3.6, 2.9 Hz).

EXAMPLE 1b 3R-(2-Phenyl-1S-methylcarbamoyl-ethylcarbamoyl)-5-methyl-2S-2-propenyl-hexanoic acid To a solution of 3R,S-(2-phenyl-1S-methylcarbamoyl-ethylcarbamoyl)-5-methyl-2S-2-propenyl-hexanoic acid-4-tert-butyl ester (4.05 g, 9.4 mmol) (10:1, SRS:RRS) in dichloromethane (25 ml) at 0° C. was added TFA (12 ml). The reaction flask was placed in the fridge for 12 hours. Excess TFA and solvent were removed under reduced pressure. The residue was taken up in dichloromethane (20 ml), and washed with brine (2×25 ml). The dichloromethane layer was dried over $MgSO_4$ and solvent removed under reduced pressure to give a white solid, which was recrystallised from ethyl acetate/hexane to yield the title compound as a white crystalline solid (3.3 g, 94%).

$^1$H-NMR; $\delta(CD_3OD)$, 8.41 (1H, d, J=7.9 Hz), 7.83 (1H, br s), 7.23 to 7.11 (5H, br m), 5.58 to 5.42 (1H, br m), 4.88 (2H, m), 4.63 (1H, m), 3.03 (1H, dd, J=8.1, 5.6 Hz), 2.84 (1H, dd, J=9.9, 3.7 Hz), 2.65 (3H, d, J=4.5 Hz), 2.48 (1H, dt, J=7.7, 2.9 Hz), 2.31 (1H, dt, J=6.8, 3.7 Hz), 1.85 (1H, m),1.52 (2H, m), 1.30 (1H, br m), 1.00 (1H, m), and 0.81 (6H, dd, J=10.3, 6.4 Hz).

EXAMPLE 1c 3R-(2-Phenyl-1S-methylcarbamoyl-ethylcarbamoyl)-5-methyl-2S-2-propenyl-hexanohydroxamic acid To a solution of 3R-(2-phenyl-1S-methylcarbamoyl-ethylcarbamoyl)-5-methyl-2S-2-propenyl-hexanoic acid (2.52 g, 6.73 mmol) in DMF (50 ml) was added HOBt (1.18 g, 8.75 mmol), NMM (0.88 g, 8.75 mmol) and EDC(1.68 g, 8.75 mmol). The reaction mixture was cooled to 0° C. and hydroxylamine hydrochloride (0.94 g, 13.5 mmol), NMM (1.36 g, 13.5 mmol) were added. The reaction mixture was allowed to warm to room temperature and stirred for 12 hours. Removal of the solvent under reduced pressure left an oil to which was added an ether water mixture (1:1,80 ml). The precipitated solid was collected by filtration then recrystallisation from methanol/diisopropyl ether yielded the title compound as a white solid (single diastereoisomer, 1.97 g, 75%).

m.p. 235°–236 ° C.

Analysis calculated for $C_{21}H_{31}N_3O_4 0.5H_2O$ Requires C 63.29, H 8.09, N 10.54 Found C 63.16, H 8.02, N 10.73

$^1$H-NMR; $\delta(CD_3OD)$, 8.51 (1H, d, J=8.0 Hz), 7.85 (1H, br s), 7.26–7.10 (5H, br m), 5.50–5.35 (1H, br m), 4.82 (2H, m), 4.64 (1H, dd, J=9.2, 5.5 Hz), 3.03 (1H, dd, J=8.4, 5.3 Hz), 2.84 (1H, dd, J=10.0, 3.6 Hz), 2.66 (3H, d, J=3.3 Hz), 2.42 (1H, m), 2.02–1.78 (2H, br m), 1.44 (3H, br m), 1.17–0.93 (1 H, br m), and 0.81 (6H, dd, J=10.6, 6.4 Hz).

$^{13}$C-NMR; $\delta(CD_3OD)$ 176.2, 173.9, 172.4, 138.5, 136.1, 130.3, 129.4, 127.9, 117.2, 56.0, 41.6, 38.9, 35.7, 26.9, 26.2, 24.4, and 21.7.

EXAMPLE 2

3R-(3-Methoxycarbonyl-1S-methylcarbamoyl-propylcarbamoyl )-5-methyl-2S-2-propenyl-hexanohydroxamic acid

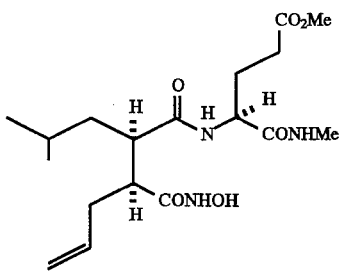

Prepared by methods analogous to those described in Example 1, starting from S-5-methylglutamic acid N-methylamide.

m.p. 228°–229° C.

$^1$H-NMR; $\delta(CD_3OD)$, 5.63 (1H, br m), 4.97 (2H, m), 4.33 (1H, m), 3.62 (3H, s), 2.68 (3H, s), 2.53 (1H, m), 2.38 (2H, t, J=7.2 Hz), 2.20 (2H, m), 2.11–1.91 (3H, br m), 1.56–1.45 (2H, br m), 1.02 (1H, m) and 0.82 (6H, dd, J=7.3, 6.2 Hz).

$^{13}$C-NMR; $\delta(CD_3OD)$, 177.2, 174.8, 173.8, 172.3, 136.0, 117.5, 53.7, 52.2, 41.6, 36.2, 31.0, 28.0, 26.9, 26.2, and 21.7.

EXAMPLE 3

3R-(1S-Methylcarbamoyl-2-thien-2-yl-ethylcarbamoyl)-5-methyl-2S-2-propenyl-hexanohydroxamic acid

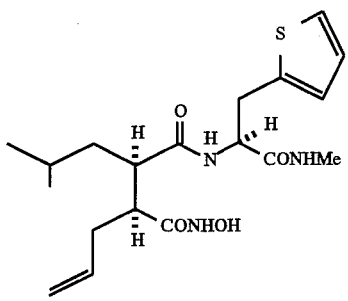

Prepared by methods analogous to those described in Example 1, starting from S-2-thienylalanine N-methylamide.

m.p. 216°–217° C.

Analysis calculated for $C_{19}H_{29}N_3O_4S.0.3H_2O$ Requires C 56.92, H 7.44, N 10.48, S 8.00% Found C 57.01, H 7.26, N 10.23, S 8.06%

$^1$H-NMR; δ(CD$_3$OD), 7.11 (1H, dd, J=1.0, 4.0 Hz), 6.87–6.79 (2H, m), 5.54–5.39 (1H, m), 4.80 (2H, m), 4.60 (1H, dd, J=6.0, 3.1Hz), 3.43–3.06 (3H, m), 2.64 (3H, s), 2.46 (1H, m), 1.99 (2H, m), 1.56 (1H, br m), 1.32 (1H, br m), 0.97 (1H, br m), 0.82 (3H, d, J=6.4 Hz), and 0.75 (3H, d, J=6.4 Hz).

$^{13}$C-NMR; δ(CD$_3$OD) 176.4, 173.3, 172.3, 140.3, 136.8, 127.8, 127.6, 125.2, 117.2, 56.2, 41.6, 35.7, 32.9, 27.0, 26.2, 24.2, and 21.8.

EXAMPLE 4

3R-(3-Methyl-1S-methylcarbamoyl-butylcarbamoyl)-5-methyl-2S-2-propenyl-hexanohydroxamic acid

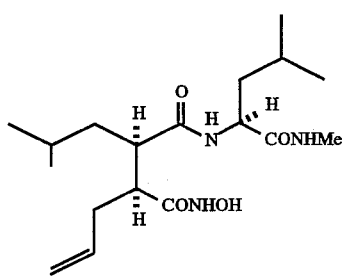

Prepared by methods analogous to those described in Example 1, starting from S-leucine N-methylamide.

m.p. 226°–228° C.

Analysis calculated for $C_{18}H_{33}N_3O_4.0.1H_2O$ Requires C 60.51, H 9.37, N 11.76% Found C 60.48, H 9.21, N 11.67%

$^1$H-NMR; δ((CD$_3$)$_2$SO, 333K), 10.32 (1H, s), 8.53 (1H, s), 7.90 (1H, d, J=7.8 Hz), 7.40 (1H, br m), 5.69–5.55 (1H, m), 4.92 (2H, m), 4.29 (1H, dd, J=8.3, 5.3 Hz), 2.57 (3H, d, J=3.7 Hz), 2.20 (2H, m), 2.00 (1H, m), 1.62 (1H, m), 1.54–1.40 (3H, m), 0.98 (1H, m), and 0.91–0.77 (12H, m).

$^{13}$C-NMR; δ((CD$_3$)$_2$SO, 333K), 173.3, 172.2, 169.4, 136.0, 115.8, 51.1, 46.2, 45.9, 34.7, 25.4, 25.3, 24.3, 23.9, 23.0, 21.6, and 21.4.

EXAMPLE 5

3R-(2,2-Dimethyl-1S-methylcarbamoyl-propylcarbamoyl)-5-methyl-2S-2-propenyl-hexanohydroxamic acid

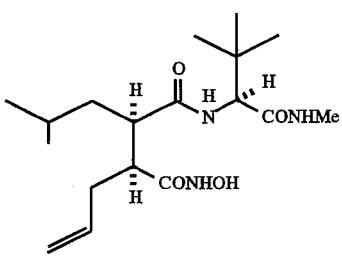

Prepared by methods analogous to those described in Example 1, starting from S-tert-leucine N-methylamide.

m.p. 229.5°–231.5° C.

Analysis calculated for $C_{18}H_{33}N_3O_4.0.2H_2O$ Requires: C 60.21, H 9.38, N 11.70% Found: C 60.34, H 9.23, N 11.61%

$^1$H-NMR; δ(CD$_3$OD), 8.05 (1H, d, J=9.0 Hz), 7.96 (1H, br s), 5.55–5.71 (1H, br m), 4.96 (2H, m), 4.23 (1H, d, J=9.0 Hz), 2.66 (4H, m and d, J=4.6 Hz), 2.03–2.33 (3H, br m), 1.48 (1H, m), 1.34 (1H, m), 0.98 (10H, s and m), 0.84 (3H, d, J=6.4 Hz) and 0.79 (3H, d, J=6.5 Hz).

$^{13}$C-NMR; δ(CD$_3$OD), 176.5, 173.0, 172.4, 136.1, 117.4, 62.5, 41.8, 36.4, 35.1, 27.3, 27.1, 26.0, 24.3 and 22.0.

EXAMPLE 6

2S-[1S-Methylcarbamoyl-2-oxadiazol-5-yl-ethylcarbamoyl)-5-methyl-2S-2-propenyl-hexanohydroxamic acid

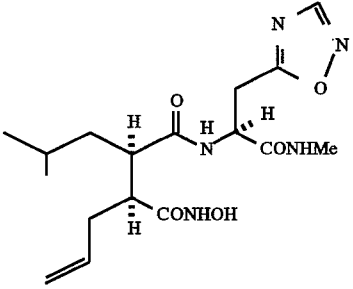

Prepared by methods analogous to those described in Example 1, starting from S-5-oxadiazolylalanine N-methylamide.

m.p. 220°–221° C.

$^1$H-NMR; δ(CD$_3$OD), 5.57 (1H, m), 5.01–4.83 (3H, m), 3.31 (2H, d, J=7.5 Hz), 2.71 (3H, s), 2.48 (1H, m), 2.25 (3H, s), 2.12 (1H, m), 2.02 (1H, m), 1.82 (1H, m) 1.50 (1H, m), 1.35 (1H, m), 1.00 (1H, m), 0.83 (3H, d, J=6.6 Hz) and 0.80 (3H, d, J=6.7 Hz).

$^{13}$C-NMR; d ((CD$_3$)$_2$SO), 176.6, 173.4, 169.8, 169.1, 166.6, 135.9, 116.0, 50.1, 45.9, 45.7, 39.7, 34.2, 28.4, 25.6, 25.2, 24.0, 21.3 and 11.1.

EXAMPLE 7

3R-(2-Phenyl-1S-phenylmethylcarbamoyl-ethylcarbamoyl)-5-methyl-2S-2-propenyl-hexanohydroxamic acid

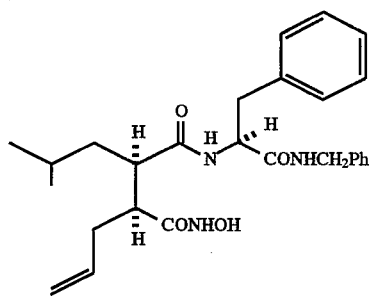

Prepared by methods analogous to those described in Example 1, starting from S-phenylalanine N-benzylamide.

m.p. 236°–237° C.

$^1$H-NMR; d (($CD_3$)$_2$SO), 8.73 (1H, d, J=1.4 Hz), 8.33 (2H, m), 7.22 (10H, m), 5.34 (1H, m), 4.81–4.65 (3H, m), 4.28 (2H, dd, J=6.2, 12.4 Hz), 2.99 (1H, dd, J=4.5, 13.7 Hz), 2.85 (1H, dd, J=4.0, 8.0 Hz), 2.50–2.48 (1H, m), 1.93–1.79 (2H, m), 1.35–1.25 (3H, m), 0.89–0.69 (1H, m), and 0.89–0.69 (6H, dd, J=6.4, 6.0 Hz).

$^{13}$C-NMR; d (($CD_3$)$_2$SO), 173.3, 171.1, 169.3, 139.1, 137.9, 135.9, 129.1, 128.1, 127.9, 127.2, 126.7, 126.2, 115.6, 54.1, 46.2, 45.8, 42.3, 37.5, 34.2, 25.2, 23.9 and 21.5.

Biological Example A

The potency of compounds of the invention as inhibitors of collagenase was determined by the procedure of Cawston and Barrett, (*Anal. Biochem.*, 99, 340–345, 1979), hereby incorporated by reference, whereby a 1 mM solution of the compound being tested, or a dilution thereof, was incubated at 37° for 16 hours with collagen and collagenase (buffered with 25 mM Hepes, pH 7.5 containing 5 mM $CaCl_2$, 0.05% Brij 35 and 0.02% $NaN_3$). The collagen was acetylated $^{14}$C collagen prepared by the method of Cawston and Murphy, (*Methods in Enzymology*, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity ($IC_{50}$).

The potency of compounds of the invention as inhibitors of stromelysin was determined by the procedure of Cawston et al, (*Biochem. J.*, 195, 159–165, 1981), hereby incorporated by reference, whereby a 1 mM solution of the compound being tested, or a dilution thereof, was incubated at 37° for 16 hours with stromelysin and $^{14}$C acetylate casein (buffered with 25 mM Hepes, pH 7.5 containing 5 mM $CaCl_2$, 0.05% Brij 35 and 0.02% $NaN_3$). The casein was acetylated $^{14}$C casein prepared by the method of Cawston et al (ibid). The stromelysin activity in the presence of 1 mM of the test compound, or a dilution thereof, was compared to activity in a control devoid of inhibitor and the result reported below as that of inhibitor concentration effecting 50% inhibition of the stromelysin activity ($IC_{50}$).

Results:

| Compound | Collagenase $IC_{50}$ (nM) | Stromelysin $IC_{50}$ (nM) |
|---|---|---|
| Example 1 | 10 | 30 |
| Example 5 | 3–4 | 80 |
| Example 7 | 10 | 5 |

Biological Example B

The biological efficacy of a compound of the invention in chronic disease states is a function of the systemic blood concentration maintained over time, and its intrinsic potency. These factors can be quantified as $IC_{50}$.hrs (24 hrs), which parameter is defined as the total number of $IC_{50}$s in the blood over the 24 hours post dosing, the $IC_{50}$ being defined as the concentration of the compound that reduces collagenase activity to 50% of its normal value.:

Test compounds were administered at 10 mg/kg in PBS/0.1% Tween 80 by gavage to 6 male rats (300 g) per treatment group. Blood samples were removed by tail venepuncture at 0.5, 1.0, 2.0, 6.0 and 24 hours post administration. 0.5 ml of blood was placed into 4.5 ml tubes containing 0.1 ml acid citrate dextrose (ACD) as anticoagulant. For extraction, 3 ml methanol was added and the precipitated blood pelletted by centrifugation (30 min at 3000 rpm). A 2 ml aliquot of supernatant was removed and dried by lyophilisation. The extract was redissolved in 200 µl DMSO and a 10 µl aliquot assayed for collagenase inhibitory activity. The inhibitory activity in the extracts was determined using the collagenase assay described in Biological Example A above, and the concentration of inhibitor (that is drug plus any active metabolites) obtained by comparison with standard curves. Results are expressed as area under the curve (AUC) $IC_{50}$.hrs (24 hrs), the $IC_{50}$ being defined as the concentration of the compound that reduces collagenase activity to 50% of its normal value.

Results

| Compound | AUC ($IC_{50}$ · hrs (24hrs)) |
|---|---|
| Example 1 | 233 |
| Example 5 | 970 |

Biological Example C

The compound of Example 1 was tested in a rat adjuvant arthritis model.

Adjuvant arthritis was produced in male Lewis rats (Charles River) by a single intradermal injection of 0.75 mg of M. butyricum in light parafin oil (Freund's complete adjuvant) into the base of the tail. The "secondary" lesion occurs after a delay of 10 days, and is characterised by inflammation of the hindpaws. Hindpaw oedema volumes were measured plethysmographically by water displacement. Animals in the treated groups received two doses of 10 mg/kg of the test compound in PBS/0.1% Tween orally, each day, from day 13 to day 17. Results are reported as paw volume change from the volume measured on day 13.

Results:

| Compound of | Day 17 | Day 20 |
| --- | --- | --- |
| Example 1 | (% relative to day 13) 52% | (% relative to day 13) 65% |

What is claimed is:

1. A compound of formula (I):

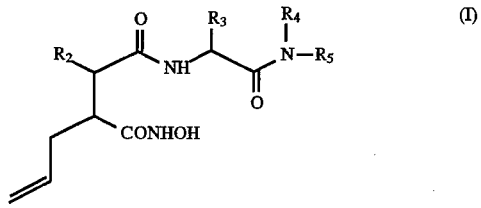

wherein $R_2$ represents a $C_2-C_6$ alkyl group which may contain an ether or thioether linkage;

$R_3$ represents (a) the side chain of a naturally occurring alpha-amino acid in which any carboxylic acid groups may be esterified or amidated, any hydroxyl or thiol groups may be acylated or alkylated (etherified) and any amino groups may be acylated, or (b) a group $R_6(A)_n$— wherein n is 0 or 1, A represents a divalent $C_1-C_6$ alkyl or $C_2-C_6$ alkenyl group optionally interrupted by one or more —O—, or —S— atoms or —N($R_7$)— groups where $R_7$ is hydrogen or $C_1-C_6$ alkyl, and $R_6$ is a phenyl or heterocyclyl group either of which may be substituted, or (except where n is 0) a hydrogen atom;

$R_4$ represents hydrogen or methyl;

$R_5$ represents hydrogen, $C_1-C_6$ alkyl or phenyl($C_1-C_6$ alkyl), or a salt, solvate or hydrate thereof.

2. A compound as claimed in claim 1 wherein the stereochemistry is as follows:

C atom carrying the allyl group and hydroxamic acid moiety is S,

C atom carrying the $R_2$ group is R,

C atom carrying the $R_3$ group is S.

3. A compound as claimed in claim 1 or claim 2 wherein $R_2$ represents an isobutyl group.

4. A compound as claimed in claim 1 or claim 2 wherein $R_3$ represents a phenylmethyl (benzyl) group in which the phenyl ring is optionally substituted with a $C_1-C_4$ alkoxy or HOOC—($C_1-C_4$ alkyl)—O— group, a thienylmethyl group, a $C_1-C_6$ alkyl group, or a $CH_2CO_2(C_1-C_4)$alkyl or $CH_2CH_2CO_2(C_1-C_4)$alkyl group.

5. A compound as claimed in claim 1 or claim 2 wherein $R_3$ represents a terbutyl group.

6. A compound as claimed in claim 1 or claim 2 wherein $R_4$ represents a hydrogen atom.

7. A compound as claimed in claim 1 or claim 2 wherein $R_5$ represents a ($C_1-C_4$)alkyl group or a benzyl group.

8. A method of treating a disease or condition mediated by MMPs and/or TNF in mammals including humans, which method comprises administering to the mammal an effective amount of a compound as claimed in claim 1 or claim 2.

9. A method as claimed in claim 8, wherein the disease or condition referred to is one mediated by an MMP.

10. A method as claimed in claim 9, wherein the disease or condition referred to is rheumatoid arthritis, osteoarthritis, periodontitis, gingivitis, corneal ulceration or tumour invasion by secondary metastases.

11. A method as claimed in claim 8, wherein the disease or condition referred to is one mediated by TNF.

12. A method as claimed in claim 11, wherein the disease or condition referred to is inflammation, fever, cardiovascular effects, haemorrhage, coagulation, acute phase response, cachexia, anorexia, an acute infection, a shock state, a graft versus host reaction or autoimmune disease.

13. A pharmaceutical or veterinary composition comprising a compound as claimed in claim 1 or claim 2 together with a pharmaceutically or veterinarily acceptable excipient or carrier.

14. A compound selected from the group consisting of 3R-(3-methoxycarbonyl-1S-methylcarbamoyl-propylcarbamoyl)-5-methyl-2S-2-propenyl-hexanohydroxamic acid;

3R-(1S-methylcarbamoyl-2-thien-2-yl-ethylcarbamoyl)-5-methyl-2S-2-propenyl-hexanohydroxamic acid;

3R-(3-Methyl-1S-methylcarbamoyl-butylcarbamoyl)-5-methyl-2S-2-propenyl-hexanohydroxamic acid;

2S-[1S-methylcarbamoyl-2-oxadiazol-5-yl-ethylcarbamoyl)-5-methyl-2S-2-propenyl-hexanohydroxamic acid;

or salts, solvates or hydrates thereof.

15. 3R-(2-Phenyl-1S-methylcarbamoyl-ethylcarbamoyl)-5-methyl-2S-2-propenyl-hexanohydroxamic acid or its salts, solvates or hydrates.

16. 3R-(2,2-Dimethyl-1S-methylcarbamoyl-propylcarbamoyl)-5-methyl-2S-2-propenyl-hexanohydroxamic or and its salts, solvates or hydrates.

17. 3R-(2-Phenyl-1S-phenylmethylcarbamoyl-ethylcarbamoyl)-5-methyl-2S-2-propenyl-hexanohydroxamic acid or its salts, solvates or hydrates.

18. A process for the preparation of a compound as claimed in claim 1 comprising:

(a) coupling an acid of general formula (II)

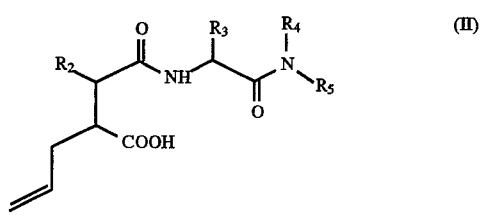

or an activated derivative thereof with hydroxylamine, O-protected hydroxylamine, or a salt thereof, $R_2$, $R_3$, $R_4$ and $R_5$ being as defined in claim 1 in relation to general formula (I) except that any substituents in $R_2$, $R_3$, $R_4$ and $R_5$ which are potentially reactive with hydroxylamine, O-protected hydroxylamine or their salts may themselves be protected from such reaction, then removing any protecting groups from the resultant hydroxamic acid moiety and from any protected substituents in $R_2$, $R_3$, $R_4$ and $R_5$; and (b) optionally converting a compound of general formula (I) into another compound of general formula (I).

19. A process as claimed in claim 18 wherein an activated derivative of a compound of formula (II) is used and said activated derivative is a pentafluorophenyl, hydroxysuccinyl, or hydroxybenztriazyl ester.

20. A process as claimed in claim 18 or claim 19 wherein the compound of general formula (II) is prepared by coupling an acid of formula (III) or an activated derivative thereof with an amine of formula (IV)

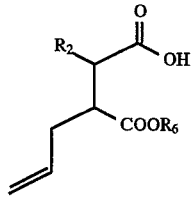 (III)

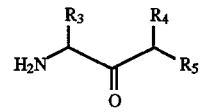 (IV)

wherein $R_2$, $R_3$, $R_4$ and $R_5$ are as defined in claim 1 in relation to general formula (I) and $R_6$ represents $C_1$14 $C_6$ alkyl, or benzyl.

* * * * *